(12) United States Patent
Hoheisel

(10) Patent No.: US 7,386,091 B2
(45) Date of Patent: Jun. 10, 2008

(54) X-RAY MAMMOGRAPHY MACHINE HAVING A DIGITAL FLAT SOLID STATE DETECTOR

(75) Inventor: Martin Hoheisel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/260,361

(22) Filed: Oct. 28, 2005

(65) Prior Publication Data

US 2006/0098777 A1 May 11, 2006

(30) Foreign Application Priority Data

Oct. 29, 2004 (DE) .................... 10 2004 052 613

(51) Int. Cl.
*A61B 6/04* (2006.01)
(52) U.S. Cl. ........................................ 378/37; 378/189
(58) Field of Classification Search ................ 378/37, 378/98.8, 197, 195, 189, 177, 181
See application file for complete search history.

(56) References Cited

U.S. PATENT DOCUMENTS 5,883,937 A    3/1999  Schmitt
6,404,852 B1 *  6/2002  Petrick et al. ............. 378/98.8
6,412,978 B1 *  7/2002  Watanabe et al. ........... 378/197
2004/0101095 A1 *  5/2004  Jing et al. ...................... 378/37
2005/0254620 A1 * 11/2005  Shoji et al. .................... 378/37

FOREIGN PATENT DOCUMENTS

DE    197 28 023 A1    1/1998

* cited by examiner

*Primary Examiner*—Hoon Song
(74) *Attorney, Agent, or Firm*—Harness, Dickey & Pierce, P.L.C.

(57) ABSTRACT

To adapt with low outlay to different patient sizes, an X-ray mammography machine is disclosed, including a digital, substantially rectangular flat solid state detector delimited by two parallel longitudinal edges and two parallel, shorter transverse edges. The flat solid state detector can be adjusted in such a way that a longitudinal edge can be positioned parallel to a chest wall of a female patient in a first position, and a transverse edge can be positioned parallel to the chest wall of the female patient in a second position.

12 Claims, 3 Drawing Sheets

X-RAY MAMMOGRAPHY MACHINE HAVING A DIGITAL FLAT SOLID STATE DETECTOR

The present application hereby claims priority under 35 U.S.C. §119 on German patent application number DE 10 2004 052 613.3 filed Oct. 29, 2004, the entire contents of which is hereby incorporated herein by reference.

FIELD

The invention generally relates to an X-ray mammography machine, having a digital flat solid state detector for example.

BACKGROUND

Cassettes based on films and foils are generally used as detectors in X-ray mammography imaging. Digital flat detectors on a solid state basis have also recently become known, these being capable of digitally reading out X-ray pictures quickly and with low outlay, and of presenting them directly after being taken. Such a flat detector is described, for example, in DE 4 321 789 A1.

In the case of detectors based on films and foils, a number of film cassettes of different size are inserted in each case into the X-ray mammography machine, and exchanged if required, in order to be able to image appropriately patients' breasts of different size.

SUMMARY

An object of at least one embodiment of the present invention is to design an X-ray mammography machine having a digital flat solid state detector in such a way that X-ray pictures of patients' breasts of different size are possible in a simple way with low outlay.

An object may be achieved according to at least one embodiment of the invention by an X-ray mammography machine having a digital flat solid state detector.

In the case of the X-ray mammography machine according to at least one embodiment of the invention having a digital, substantially rectangular flat solid state detector delimited by two parallel longitudinal edges and two parallel, shorter transverse edges connecting these, owing to the provision of the possibility of adjusting in a simple way and with low outlay a single flat detector takes over the task of two flat detectors of different format by virtue of the fact that X-ray pictures of relatively large breasts are rendered possible by a first position in which a longitudinal edge runs parallel to a chest wall of the patient, and by virtue of the fact that X-ray pictures of relatively small breasts are rendered possible with only one flat solid state detector by a second position in which a shorter transverse edge runs parallel to the chest wall of the patient.

In a way that is advantageous for a particularly simple implementation of the adjustment of the flat detector, a pivotable holder of the flat detector is provided for adjusting the flat detector.

According to a refinement of at least one embodiment of the invention having circuits arranged on at least some of the edges of the flat solid state detector, for the purpose of being manipulable in practice the circuits are provided only on one of the longitudinal edges or on one of the transverse edges such that the longitudinal edge or transverse edge respectively remaining can be guided up as far as the chest wall. Owing to the fact that the active surface of the flat detector extends in this case up to the respectively remaining longitudinal edge or transverse edge, there is no difficulty in also being able to carry out a recording of breast tissue near the chest wall, something which is of great significance for a comprehensive diagnosis. The circuits are generally provided for the purpose of reading out the digital imaging data from pixel elements of the flat solid state detector, or for driving the pixel elements of the flat solid state detector. The active surface is understood to be the region of the flat detector that is sensitive to incident X radiation and on which detection can take place. Small tolerances of the distance of the active surface from the edges of the flat detector of up to 6 mm can be permitted.

It is advantageously provided in the case of an X-ray mammography machine having an X-ray tube for generating a beam in the respective position of the flat solid state detector to irradiate the active surface of the flat detector by the beam. It is thereby ensured that the entire active surface can be sensed by X radiation even after a change in position from a first position into a second one, or from a second into a first position of the flat solid state detector. This can be implemented, for example, by an automatic diaphragm control in conjunction with alterations in position.

In order to save time and outlay with exposure objects that do not fill up the detector surface, it is provided to read out from sub-regions of the active surface of the solid state detector in the case of an X-ray mammography machine having read out circuits arranged at least one edge of the flat detector.

BRIEF DESCRIPTION OF THE DRAWINGS

The invention and further advantageous refinements are explained below in more detail with the aid of schematic example embodiments in the drawings without thereby limiting the invention to these example embodiments; in the drawings.

DETAILED DESCRIPTION OF THE EXAMPLE EMBODIMENTS

Figure 1:
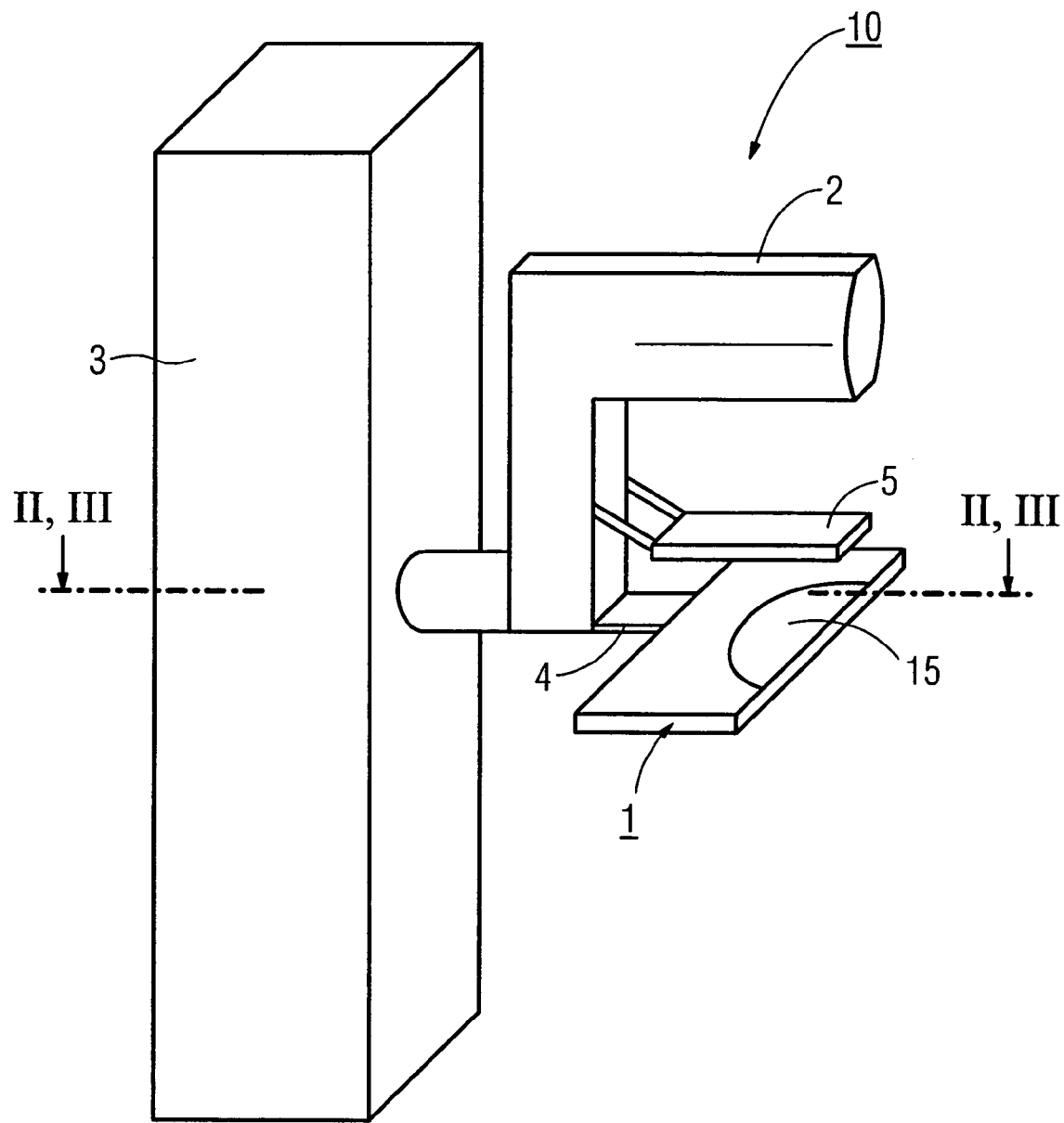
FIG. 1 shows an X-ray mammography machine having a flat solid state detector according to the prior art.

FIG. 1 shows a known X-ray mammography machine 10 having a flat solid state detector 1 fastened on a holder 4, and an X-ray tube 2 for generating an X radiation, the X-ray mammography machine 10 being fastened on a stand 3 for stabilization. A breast 16 of a patient that is to be imaged is compressed by a compression plate 5 and imaged by the X radiation of the X-ray tube 2 onto the flat solid state detector 1. Drive circuits drive the pixel elements of the flat solid state detector, and the X-ray image is read out by read out circuits, transmitted for processing to an evaluation unit (not shown), and represented on a display (not shown).

Figure 2:
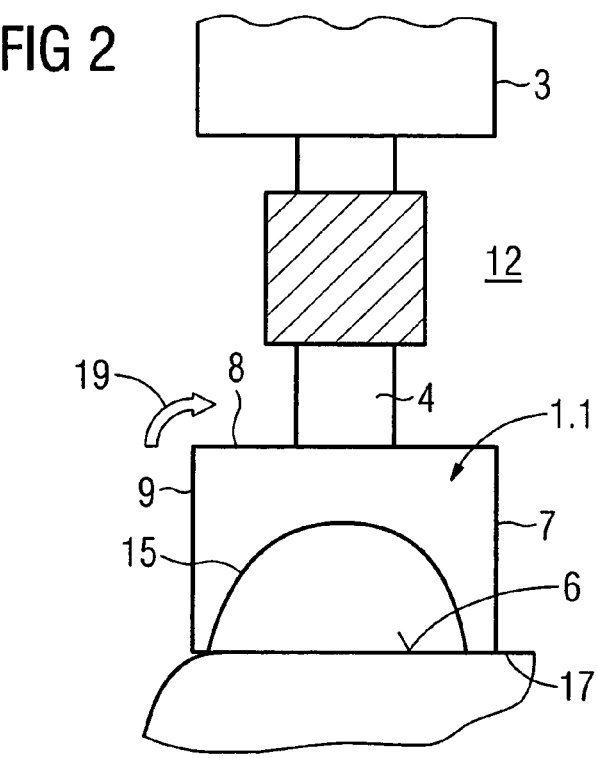
FIG. 2 shows a plan view of an X-ray mammography machine according to the invention having an adjustable flat solid state detector in a first position.
Figure 3:
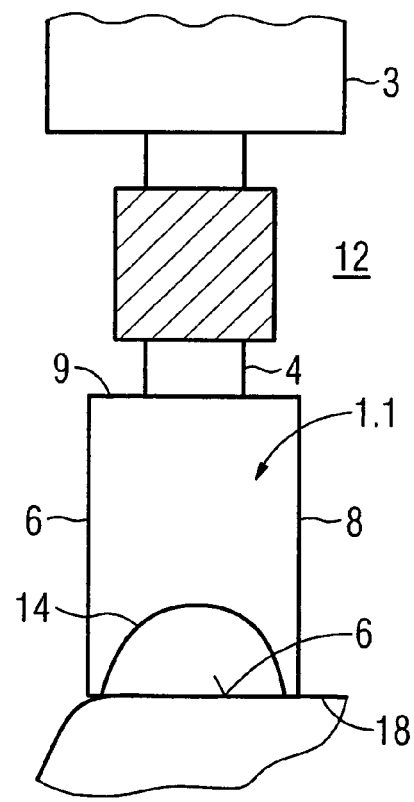
FIG. 3 shows a plan view of an X-ray mammography machine according to the invention having the adjustable flat solid state detector in accordance with FIG. 2 in a second position.

Shown in FIG. 2 and FIG. 3 as plan views of a section in accordance with the cutting sequence of II, III-II, III in FIG. 1 is an X-ray mammography machine 12 according to at least one embodiment of the invention having an adjustable rectangular flat solid state detector 1.1 with a first and, parallel thereto, second longitudinal edge 6 and 8, respectively, and a first and, parallel thereto, second transverse edge 7 and 9, respectively, in settings differing from one another. The flat solid state detector 1.1 can have, for example, the format of 25.1 cm times 28.7 cm.

In a first position—indicated in FIG. 2—the two longitudinal edges 6 and 8 are parallel to a chest wall 17 of a female patient (not shown), the first longitudinal edge 6 being closer to the chest wall 17, for example. This first position is preferably suitable for an X-ray picture of a relatively large breast 15.

The flat detector is brought into a second position—indicated in FIG. 3—by an adjustment, for example by a pivotable holder or by rotating the flat detector in the direction indicated by the arrow 19. In this position, the transverse edges 7 and 9 are parallel to the chest wall 18 of a female patient, the first transverse edge 7 being closer to the chest wall 18, for example. This position is preferably suitable for X-raying a small breast 14.

Substantial costs can be saved by virtue of the fact that only a single flat solid state detector is required for the X-ray mammography machine 12 instead of two such detectors of different format.

Figure 4:
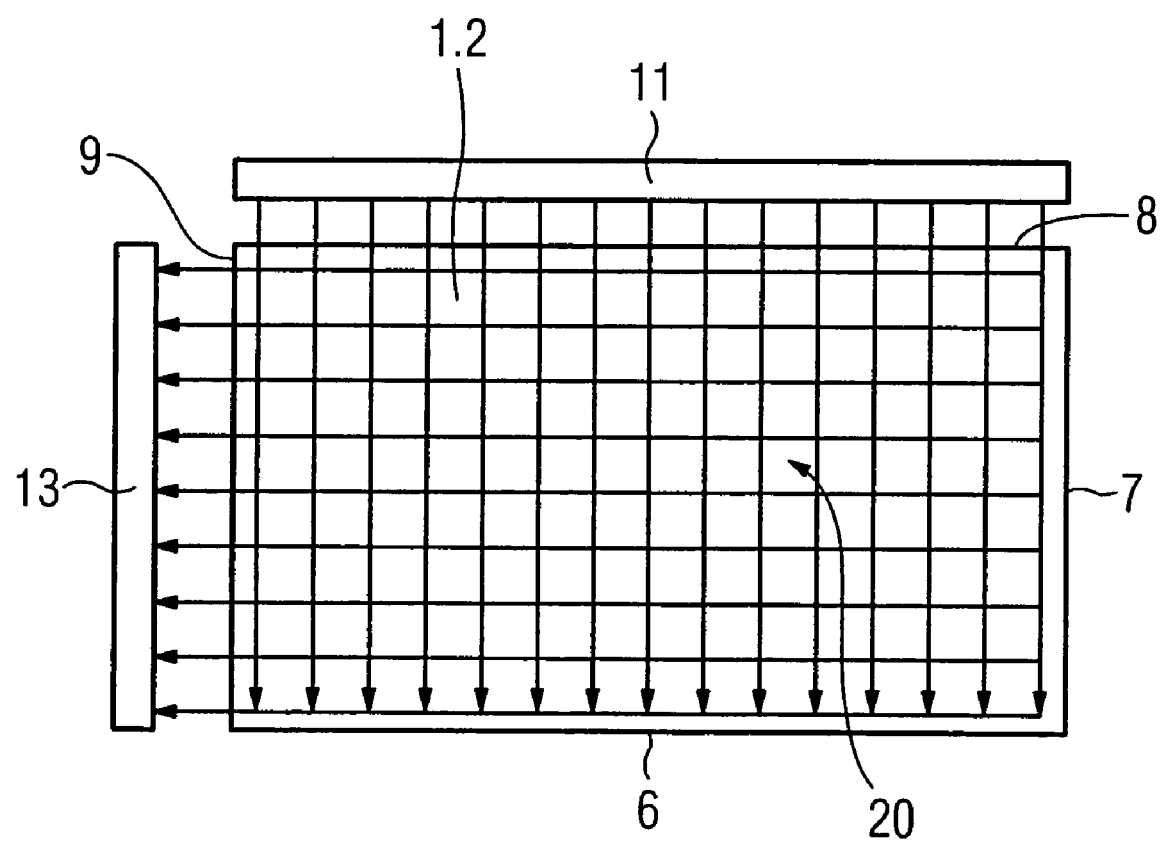
FIG. 4 shows a flat solid state detector having single-sided read out circuits.

FIG. 4 shows a flat solid state detector 1.2 that is particularly suitable for the X-ray mammography machine 12 according to at least one embodiment of the invention and has drive circuits 11 arranged on a second longitudinal edge 8, and read out circuits 13 arranged on a second transverse edge 9. Owing to the fact that the active surface 20 of the flat solid state detector 1.2 reaches up to the respective other first longitudinal edge 6 and first transverse edge 7, these edges are preferably suitable for bordering directly on the respective chest wall 17; 18. By comparison with a known flat solid state detector having read out circuits arranged on two sides for example on the two transverse edges 7; 9, a flat solid state detector 1.2 having read out circuits 13 arranged on one side has the advantage, furthermore, of being more cost effective because of the lesser number of circuits. It can also be provided to fit the drive circuits 11 on a second transverse edge 9, and the read out circuits 13 on a second longitudinal edge 8. It is also possible, furthermore, to use a flat detector 1.1 having two-sided circuits for the X-ray mammography machine 12 if the circuits are no more than 6 mm in their longitudinal extent.

In the position in which the transverse edges 7 and 9 are arranged parallel to the chest wall 18, it is possible to dispense with reading out a reading of the flat solid state detector 1.1; 1.2 averted from the female patient when the small breast 14 to be examined does not extend as far as into this region. The outcome of this is that the data volume to be read out and to be transmitted to an evaluation unit is reduced by comparison with an entire image, and the processing time is shortened. The adjustment into a second position in which the transverse edges 7 and 9 are arranged parallel to the chest wall 17; 18 is, however, particularly suitable for MLO (medio-lateral-oblique) pictures, that is to say oblique pictures of a small or large breast 14; 15, on account of the good accessibility thus ensured.

In addition, it is advantageously provided for an X-ray mammography machine 12 having a display representation of X-ray images read out from the flat solid state detector that the X-ray images can be represented in the same alignment despite different positions of the flat solid state detector 1.1; 1.2; it is possible thereby for the examining doctor to see the customary mode of representation. Thus, for example, a change in position of the flat solid state detector 1.1; 1.2 can pass on a signal to an evaluation unit connected to the X-ray mammography machine 12, which evaluation unit undertakes, automatically if necessary, to rotate the resulting X-ray image on a display under the control of software.

At least one embodiment of the invention can be summarized briefly in the following way: In order to adapt with low outlay to different patient sizes, it is provided in the case of an X-ray mammography machine 12 having a digital, substantially rectangular flat solid state detector 1.1; 1.2 delimited by two parallel longitudinal edges 6; 8 and two parallel, shorter transverse edges 7; 9 connecting these that the flat detector 1.1; 1.2 can be adjusted in such a way that a longitudinal edge 6 or 8 can be adjusted parallel to a chest wall 17; 18 of a female patient in a first position, and a transverse edge 7 or 9 can be adjusted parallel to the chest wall 17; 18 of the female patient in a second position.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray mammography machine comprising:
   a digital, substantially rectangular flat solid state detector, including two parallel longitudinal edges and two parallel, shorter transverse edges connecting the two parallel longitudinal edges, a longitudinal edge being positionable parallel to a chest wall of the patient in a first position, and a transverse edge being positionable parallel to the chest wall of the patient in a second position;
   a pivotable holder for adjusting the flat solid state detector between the first position and the second position;
   a breast compression plate for compressing a breast for imaging; and
   circuits arranged on at least some of the edges of the flat solid state detector, the circuits being provided only on one of the longitudinal edges or the transverse edges in such a way that the respective remaining longitudinal edge or transverse edge is guidable up as far as the chest wall.

2. The X-ray mammography machine as claimed in claim 1, comprising:
   an X-ray tube for generating a beam, a complete irradiation of an active surface of the flat solid state detector by the beam being provided in the respective position of the flat solid state detector.

3. The X-ray mammography machine as claimed in claim 2, comprising:
   read out circuits arranged at at least one of the edges of the flat solid state detector, to read out digital imaging data from subregions of the active surface of the flat solid state detector.

4. The X-ray mammography machine as claimed in claim 2, comprising:
   a display representation of X-ray images read out from the flat solid state detector, the X-ray images being representable in the same alignment despite different positions of the flat solid state detector.

5. The X-ray mammography machine as claimed in claim 1, comprising:

read out circuits arranged at at least one of the edges of the flat solid state detector, to read out digital imaging data from sub-regions of the active surface of the flat solid state detector.

6. The X-ray mammography machine as claimed in claim 1, comprising:
a display representation of X-ray images read out from the flat solid state detector, the X-ray images being representable in the same alignment despite different positions of the flat solid state detector.

7. The X-ray mammography machine as claimed in claim 1, comprising:
a display representation of X-ray images read out from the flat solid state detector, the X-ray images being representable in the same alignment despite different positions of the flat solid state detector.

8. The X-ray mammography machine of claim 1, wherein the read-out circuits are arranged on only one longitudinal or transverse edge.

9. An X-ray mammography machine comprising:
a digital, substantially flat solid state detector, including two parallel first edges and two parallel, shorter second edges, at least one first edge being adjustable to be positioned parallel to a chest wall of the patient in a first position, and at least one second edge being adjustable to be positioned parallel to the chest wall of the patient in a second position;
a pivotable holder for adjusting the flat solid state detector between the first position and the second position;
a breast compression plate for compressing a breast for imaging; and
circuits arranged on at least some of the edges of the flat solid state detector, the circuits being provided only on one of the first edges or the second edges in such a way that the respective remaining first edge or second edge is guidable up as far as the chest wall.

10. The X-ray mammography machine as claimed in claim 9, comprising:
an X-ray tube for generating a beam, a complete irradiation of an active surface of the flat solid state detector by the beam being provided in the respective position of the flat solid state detector.

11. The X-ray mammography machine as claimed in claim 9, comprising:
read out circuits arranged at at least one of the edges of the flat solid state detector, to read out digital imaging data from sub-regions of the active surface of the flat solid state detector.

12. The X-ray mammography machine as claimed in claim 9, comprising:
a display representation of X-ray images read out from the flat solid state detector, the X-ray images being representable in the same alignment despite different positions of the flat solid state detector.

* * * * *